United States Patent [19]
Smith

[11] Patent Number: 5,856,489
[45] Date of Patent: Jan. 5, 1999

[54] PROCESS FOR THE PRODUCTION OF AMINOAZOBICYCLOALKANES FROM OXIMES

[75] Inventor: Gillian Elizabeth Smith, Hertfordshire, England

[73] Assignee: SmithKline Beecham p.l.c., Brentford, England

[21] Appl. No.: 776,451

[22] PCT Filed: Jul. 18, 1995

[86] PCT No.: PCT/EP95/02824

§ 371 Date: Jan. 23, 1997

§ 102(e) Date: Jan. 23, 1997

[87] PCT Pub. No.: WO96/03401

PCT Pub. Date: Feb. 8, 1996

[30] Foreign Application Priority Data

Jul. 23, 1994 [GB] United Kingdom .................. 9414900

[51] Int. Cl.$^6$ ...................... C07D 221/22; C07D 451/02; C07D 451/14
[52] U.S. Cl. .......................... 546/112; 546/124; 546/125; 546/126
[58] Field of Search ...................... 546/112, 124, 546/125, 126

[56] References Cited

U.S. PATENT DOCUMENTS

| | | | |
|---|---|---|---|
| 4,432,983 | 2/1984 | Riley et al. | 424/265 |
| 5,344,940 | 9/1994 | Domagala | 548/540 |

FOREIGN PATENT DOCUMENTS

| | | |
|---|---|---|
| 79302978 | 12/1979 | European Pat. Off. . |
| 81302630 | 6/1981 | European Pat. Off. . |
| 33 22 574.5 A1 | 6/1983 | Germany . |

OTHER PUBLICATIONS

Bermudez J et al. J. Med. Chem. 33(7), pp. 1925–1929, 1990.

N. Cabezas, et al., J. Mol. Struct. vol. 172, 1988; pp. 381–394.

M.S. Newman, V. Lee, J. Org. Chem. vol. 40, No. 3, 1975; pp. 381–382.

*Primary Examiner*—Evelyn Huang
*Attorney, Agent, or Firm*—Wayne J. Dustman; Charles M. Kinzig; Edward T. Lentz

[57] ABSTRACT

A process for preparing a compound of formula (I), wherein n is 2 or 3; which process comprises reducing a compound of formula (II), wherein $R^1$ is hydrogen or $C_{1-4}$ alkyl and n is 2 or 3; by catalytic hydrogenation in the presence of a rhodium catalyst.

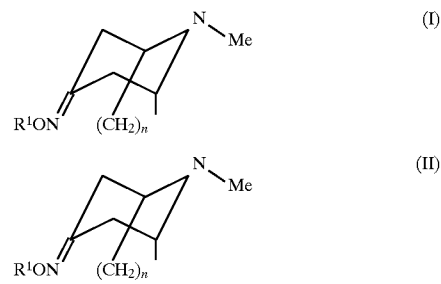

10 Claims, No Drawings

PROCESS FOR THE PRODUCTION OF AMINOAZOBICYCLOALKANES FROM OXIMES

This application is the national phase of PCT/EP95/02824, filed Jul. 18, 1995, issued as WO96/03401 on Feb. 8, 1996.

The present invention relates to a new process for preparing key intermediates to pharmaceutically active compounds.

U.S. Pat. No. 4,886,808 and EP-A-247266 (Beecham Group plc) describe certain compounds which are granatane and tropane derivatives having 5-$HT_3$ receptor antagonist activity which are described as possessing a number of potential therapeutic utilities, including inter alia the treatment of cytotoxic agent induced emesis. Example 6 of U.S. Pat. No. 4,886,808 describes the preparation of granisetron, which is a granatane derivative and Example 5 of EP-A-247266 describes the preparation of BRL 46470A, which is a tropane derivative.

GB 2125398 (Sandoz Limited) describes the preparation of granatyl amines from the corresponding oxime using alane. The use of alane on a large industrial scale is disadvantageous, because it is usually generated by the addition of concentrated sulphuric acid to lithium aluminium hydride, and is a potentially hazardous reducing agent, requiring special precautionary measures.

The method described in EP-A-247266 for preparing the tropane side chain intermediate results in the formation of a considerable amount of the unwanted exo product. A new process has been devised which is convenient to use on an industrial scale, has a rapid reaction rate and results in a high ratio of desired endo product.

Accordingly, the present invention provides a process for preparing a compound of formula (I):

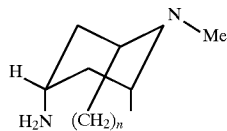

(I)

wherein
n is 2 or 3;
which process comprises reducing a compound of formula (II):

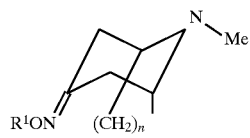

(II)

wherein $R^1$ is hydrogen or $C_{1-4}$ alkyl and n is 2 or 3; by catalytic hydrogenation in the presence of a rhodium catalyst.

Examples of $R^1$ when $C_{1-4}$ alkyl include methyl, ethyl, propyl and butyl, in all possible isomers. Preferably $R^1$ is hydrogen or methyl.

Preferably n is 2.

The catalytic hydrogenation is normally carried out in an organic solvent such as dry methanol, industrial methylated spirits, ethanol and isopropanol or an aqueous/organic solvent mixture such as in aqueous methanol, industrial methylated spirits, ethanol and isopropanol at elevated temperature such as 25° to 70° C. preferably about 50° C. and at elevated pressure such as 20 to 200 psi (137.9 to 1379 kPa), preferably at 25 to 50 psi (172.4 to 344.8 kPa). The rhodium catalyst is usually used on a conventional support medium such as carbon.

The percentage of rhodium to carbon is usually 1 to 10% by weight, preferably around 5%. The catalyst is usually used in a proportion of 1 to 20% by weight of the starting material, preferably at about 10%.

The reaction is optionally carried out in the presence of ammonia which may be added as an aqueous solution or as dry ammonia gas. The addition of ammonia gives a faster, cleaner reaction and reduces the formation of side products. Ammonia is usually added at a molar ratio of 2:1 to 15:1 to the starting material, preferably at a molar ratio of about 9:1.

Compounds of formula (II) are prepared according to conventional procedures, such as those described in Descriptions 1, 2 and 3.

The following Examples illustrate the present invention.

Description 1

Preparation of O-methyl-8-methyl-8-azabicyclo[3.2.1]octan-3-one oxime

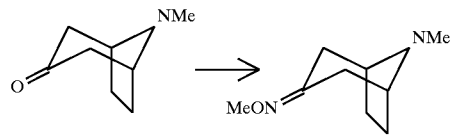

A mixture of 8-methyl-8-azabicyclo[3.2.1]octan-3-one (tropinone) (98.7 g, 0.71 mole), O-methylhydroxylamine hydrochloride (71.0 g, 0.85 mole) and water (215 ml) was stirred at ambient temperature for 0.5 h. The clear solution was basified to pH 12 with 40% aqueous NaOH and extracted with toluene (3×400 ml). The combined organic phase was dried ($K_2CO_3$), filtered and the solvent removed in vacuo. The residue was purified by fractional distillation under reduced pressure to afford the title compound as a colourless oil, 111.1 g (93%).

$^1$H NMR (CDCl$_3$, JEOL 270 MHz): δ1.50 (m,2H), δ2.05 (m,4H), δ2.37 (s,3H), δ2.55 δ(m,1H), δ3.27 (m, 2H) and δ3.80 (s, 3H). Mass Spec (JEOL DX 303) CI; m/z 168 (M$^+$), 137, 96, 82, 42.

Description 2

Preparation of 8-methyl-8-azabicyclo[3.2.1]octan-3-one oxime

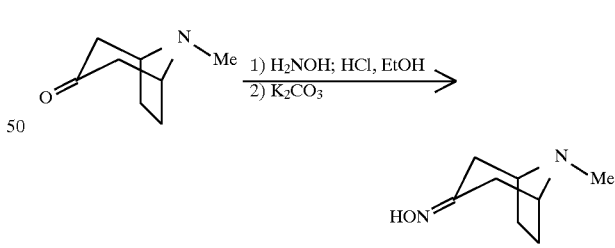

A solution of 8-methyl-8-azabicyclo[3.2.1]octan-3-one (tropinone) (2.0 kg) in industrial methylated spirits (IMS) (9.0 L) was treated portion-wise with hydroxylamine hydrochloride (1.2 kg). The resulting suspension was stirred and heated at reflux for 2 hours then allowed to cool to ambient temperature. The product. 8-methyl-8-azabicyclo[3.2.1]octan-3-one oxime hydrochloride, was filtered, washed with IMS (1.0 L) and dried in air.

The hydrochloride salt obtained above was suspended in water (11.5 L) and dichloromethane (5.0 L) and treated with potassium carbonate (3.9 kg). The organic layer was separated and the aqueous layer was extracted twice with dichloromethane (3.0 L and 2.0 L). The combined organic extracts were dried with potassium carbonate, filtered through CELITE and the solvent evaporated. The residue was triturated with ethyl acetate (2.0 L), filtered and dried under vacuum to give the title compound (1.93 kg, 87%), as a white solid $^1$H NMR (CDCl$_3$, JEOL 270 MH$_z$): δ11.1 (br s,1H), δ3.3 (m,2H), δ3.0 (d, 1H), δ2.65 (dd, 1H), δ2.4 (s, 3H), δ2.25 (dd, 1H), δ2.15 (d, 1H), δ2.0 (m, 2H), δ1.55 (m, 2H).

$^{13}$C NMR (CDCl$_3$, JEOL 67.8 MHz): δ26.1(CH$_2$), δ27.0 (CH$_2$), δ30.8 (CH$_2$), δ36.8 (CH$_2$), δ38.8 (CH$_2$), δ59.8 (CH), δ60.5 (CH), δ154.5 (quat), Mass Spec (JEOL DX303) EI: m/z 154, (M$^+$) 137, 96, 82, 42.

Description 3

Preparation of 9-methyl-9-azabicyclo[3.3.1]nonan-3-one oxime

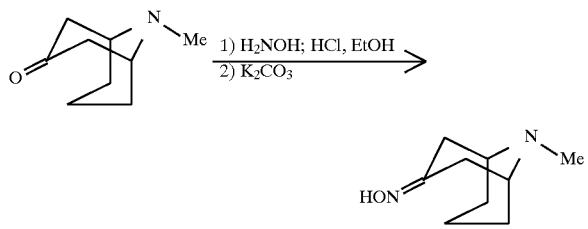

9-Methyl-9-azabicyclo[3.3.1]nonan-3-one (77 g,: Org. Synth Coll Vol. 4, 816) was added to a suspension of hydroxylamine hydrochloride (41.7 g) in ethanol (350 mls). The mixture was heated at reflux for 2 hours, then allowed to cool to ambient temperature. The product solid was filtered, washed with ethanol (50 ml) then diethylether (200 ml) and dried in air.

The hydrochloride salt obtained above was suspended in water (390 ml and dichloromethane (110 ml) and treated with potassium carbonate (49.1 g). The organic layer was separated and the aqueous phase was extracted twice with dichloromethane (2×110 ml).

The combined organic extracts were dried with potassium carbonate whilst stirring with activated charcoal.

The mixture was filtered through CELITE and the solvent removed by evaporation under reduced pressure to give the crude free base (weight yield=34.3 g).

The crude free base was recrystallised from hot ethyl acetate (144 ml) to give the title compound as a pale yellow solid (26 g, 31%).

$^1$H NMR (CDCl$_3$, JEOL 270 MHz): δ9.62 (br s,1H), δ3.1 (m,2H), δ3.0 (s,1H), δ2.75 (dd,1H), δ2.55 (s,3H), δ2.4 (dd,1H), δ2.23 (d, 1H), δ1.95 (m,2H), δ1.75 (m,1H) δ1.5 (m,3H).

EXAMPLE 1

Preparation of endo-3-amino-8-methyl-8-azabicyclo[3.2.1]octane

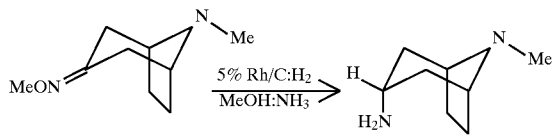

A solution of O-methyl-8-methyl-8-azabicyclo[3.2.1]octan-3-one oxime(500 g; 3 moles) in methanol (3.2 L) and 0.88 ammonia (1.8 L. 9. equivs) was hydrogenated over 5% rhodium on carbon paste (50 g dry wt.) at 35–50 psi (241.3–344.8 kPa) and 50° C. for 16 hours. After cooling and purging with nitrogen, the catalyst was filtered off and washed with fresh methanol (2×500 ml). The solvent was distilled out and the residue diluted with isopropanol (1.5 L). The solvent was again distilled out to leave the title compound as an oil which was distilled (bp 86°/7 mm) to give the purified title compound as a colourless solid (344 g, 82%).

$^1$H NMR (CDCl$_3$, JEOL 270 MHz): δ3.2 (t,1H), δ3.1 (m,2H), δ2.25 (s,3H), δ2.1 (m,2H), δ2.0 (m,4H) δ1.45 (dd,2H).

$^{13}$C NMR (CDCl$_3$; JEOL 67.8 MHz): δ26.2 (CH$_2$); δ39.4 (CH$_2$); δ40.4 (CH or CH$_3$); δ42.7 (CH or CH$_3$); δ60.3 (CH or CH$_3$) Mass Spec. (JEOL DX303) EI: m/z 140 (M$^+$), 124, 96, 83.

EXAMPLE 2

Preparation of endo-3-amino-8-methyl-8-azabicyclo[3.2.1]octane

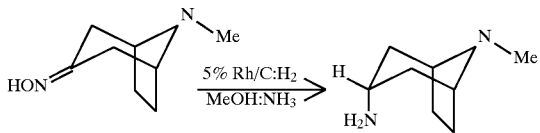

A solution of 8-methyl-8-azabicyclo[3.2.1]octan-3-one oxime (1500 g; 9.7 moles) in methanol (8.2 L) and 0.88 ammonia (5.4 L 9. equivs) was hydrogenated over 5% rhodium on carbon paste (50 g dry wt.) at 29–44 psi (199.8–303.4 kPa) and 50° for 17 hours. After cooling and purging with nitrogen, the catalyst was filtered off and washed with fresh methanol (2×1.5 L). The solvent was distilled out and the residue diluted with isopropanol (4 L). The solvent was again distilled out to leave the title compound as an oil which was distilled (bp 68°–70°/5 mm) to give the purified title compound as a colourless solid (1.23 Kg, 90%).

$^1$H NMR (CDCl$_3$, JEOL 270 MHz): δ3.2 (t,1H), δ3.1 (m,2H), δ2.25 (s,3H), δ2.1 (m,2H), δ2.0 (m,4H) δ1.45 (dd,2H).

$^{13}$C NMR (CDCl$_3$; JEOL 67.8 MHz): δ26.2 (CH$_2$); δ39.4 (CH$_2$); δ40.4 (CH/CH$_3$); δ42.7 (CH/CH$_3$); δ60.3 (CH/CH$_3$) Mass Spec. (JEOL DX303) EI; m/z 140 (M$^+$), 124, 96, 83.

EXAMPLE 3

Preparation of endo-3-amino-9-methyl-9-azabicyclo [3.3.1]nonane

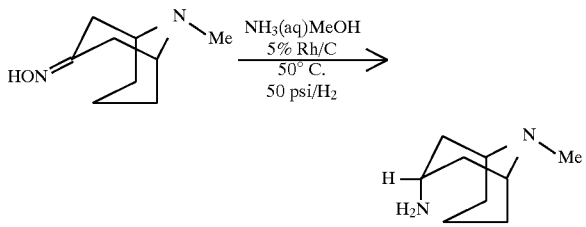

A solution of 9-methyl-9-azabicyclo[3.3.1]nonan-3-one oxime (10 g, 0.06 moles) in methanol (70 ml) and 0.88 ammonia; (36 ml; 10.0 equivs) was hydrogenated at 50° C. and 50 psi (344.8 kPa)/$H_2$ for 16 hrs using 5% Rhodium on carbon paste (1 g dry weight). The reaction mixture was cooled to room temperature and filtered to remove catalyst. The catalyst bed was washed with methanol and the methanolic solution was then evaporated under reduced pressure to give the title compound as an oil (8.6 g, 93% weight recovery) which solidified to a waxy solid on standing (8.6 g, 93%).

G.C./Mass Spec. (JEOL DX303) EI: M/z 154 ($M^+$)

I claim:

1. A process for preparing a compound of formula (I):

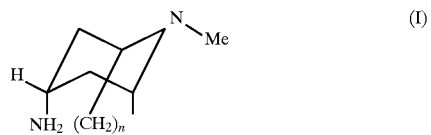

wherein n is 2 or 3;

which process comprises reducing a compound of formula (II):

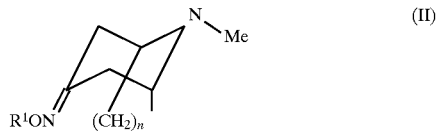

wherein $R^1$ is hydrogen or $C_{1-4}$ alkyl and n is 2 or 3; by catalytic hydrogenation in the presence of a rhodium catalyst, provided that the yield of the undo isomer is about 82% or greater.

2. A process according to claim 1 wherein n is 3.

3. A process according to claim 1 wherein n is 2.

4. A process according to claim 1 wherein $R^1$ is hydrogen or methyl.

5. A process according to claim 1 wherein the catalytic hydrogenation is carried out at elevated temperature 25° to 70° C. and at elevated pressure 20 to 200 psi (137.9 to 1379 kPa).

6. A process according to claim 5 carried out at about 50° C. and at 25 to 50 psi (172.4 to 344.8 kPa).

7. A process according to claim 1 wherein the rhodium catalyst is supported on carbon.

8. A process according to claim 1 wherein the reaction is carried out in the presence of ammonia.

9. The process of claim 1 further comprising reacting the prepared compound of formula (I) with a carboxylic acid or activated carboxylic acid to form the corresponding amide derivative.

10. A process according to claim 9 for the preparation of granisetron where the carboxylic acid is 1-methylindazole-3-carboxylic acid or an activated carboxylic acid thereof;

and optionally forming a pharmaceutically acceptable salt thereof.

* * * * *